United States Patent [19]

Harendza-Harinxma

[11] Patent Number: 4,847,283

[45] Date of Patent: * Jul. 11, 1989

[54] OINTMENT AND METHOD FOR TREATING SKIN LESIONS DUE TO HERPES VIRUS

[76] Inventor: Alfred J. Harendza-Harinxma, 50 Merion Place, Lawrenceville, N.J. 08648

[ * ] Notice: The portion of the term of this patent subsequent to Jun. 9, 2004 has been disclaimed.

[21] Appl. No.: 60,937

[22] Filed: Jun. 9, 1987

Related U.S. Application Data

[63] Continuation-in-part of Ser. No. 691,832, Jan. 16, 1985, Pat. No. 4,672,074, which is a continuation-in-part of Ser. No. 456,542, Jan. 10, 1983, abandoned.

[51] Int. Cl.$^4$ ............................................. A61K 31/405
[52] U.S. Cl. .................... 514/415; 514/418; 514/419; 514/887
[58] Field of Search ............... 514/415, 420, 145, 418, 514/419

[56] References Cited

U.S. PATENT DOCUMENTS

| | | | |
|---|---|---|---|
| 3,838,167 | 9/1974 | Jones | 548/492 |
| 4,263,313 | 4/1981 | Eckert et al. | 424/273 P |
| 4,309,414 | 1/1982 | Inagi et al. | 424/81 |
| 4,543,360 | 9/1985 | von Angerer et al. | 514/415 |
| 4,672,074 | 6/1987 | Harendza-Harinxma | 514/420 |

OTHER PUBLICATIONS

Inglot et al., Arch. Immunol. Ther. Exp; 1971 19(4) 555–66.
Chemical Abstracts 74:57306m.
Chemical Abstracts 85:99193e (1976).
Merck Index–9th ed, 1976; p. 656, 914840.

Primary Examiner—Leonard Schenkman
Attorney, Agent, or Firm—Alan M. Sack

[57] ABSTRACT

An ointment containing Indole or an Indole derivative such as Indican or Indomethacin as the active ingredient and a base. Also, a process for treating inflammations and lesions on the human skin including the step of applying an ointment containing the ointment to the lesion.

26 Claims, No Drawings

OINTMENT AND METHOD FOR TREATING SKIN LESIONS DUE TO HERPES VIRUS

This is a continuation-in-part application Ser. No. 691,832 by the same inventor, filed on Jan. 16, 1985, issued on June 9, 1987 as U.S. Pat. No. 4,672,074 which is a continuation-in-part of application Ser. No. 456,542, filed on Jan. 10, 1983 which has been abandoned.

BACKGROUND OF THE INVENTION

1. Field of the Invention

This invention relates to compositions containing indole and indole derivatives, and a method for treatment of inflamation caused by herpes virus, including herpes zoster, herpes simplex I and herpes simplex II, using the aforesaid compositions.

2. Background of the Related Art

Since the middle ages, physicians have used urine for healing of various infectious diseases. The medical reference book *Studio Medico-Chiurgico*, by Dr. Samuel Schaarschmidt, published in 1760 reveals, at pages 348-349 that lesions caused by Gonorrhea may be healed in their early stages by washing the lesions repeatedly with urine, lime water or a mixture of both. The treatment and prevention of venereal infections using urine, continued until the end of World War II. During that time, physicians advised soldiers to urinate after intercourse and if possible to wash their penis with urine.

The use of urine as a remedy to treat and prevent infectious diseases inspired the inventor to investigate the therapeutic qualities of the constituents of urine.

The Table of Urinary Values, in the *CRC Handbook of Clinical Laboratory Data* (Second Edition 1968) published by the Chemical Rubber Company (CRC) at pages 17 through 20 shows that urine specimens collected over a 24 hour period contained the following indole derivatives:

| Indole or Indole Derivative | Amount Collected per 24 hr. period |
| --- | --- |
| 5-Hydroxyindole acetic acid | 2-9 mg |
| Indican (3-Indoxylsulfate potassium salt) | 40-150 mg |
| Indole-total | 240-350 mg |
| Indole-3-acetic acid-free | 4-8 mg |
| Indole-3-acetic acid-total | 6-13 mg |
| Nicotinic acid, a product of inodole derivatives | 1160-1540 ug/liter |

The concentration of indican in urine varies between 40 and 150 mg per 24 hour period. This variation in the concentration of indican, indole and other indole derivatives in urine caused a large variation in the therapeutic results which were observed when lesions were treated using urine. The therapeutic value of a 40 mg-per 24 hours concentration of indican in urine does not provide any significant healing of a lesion, however, a concentration of 150 mg per 24 hours of indican in urine may have very good healing power.

The discovery and identification of indole and its derivatives in urine has proceeded as follows:

1. Indole was first prepared by Weissgerber in 1910 (Ber. 43, 3520, 1910). It was was identified in urine by Seifer, A. and Gerstenfeld, S. in 1964 (Clin. Chem., 10, 321, 1964).

2. Indican was first prepared by Baeyer (Ber. 14, 1745, 1881). It was first identified in urine by Sharlit, H. in 1932 (J. Biol. Chem. 99, 537, 1932).

3. Nicotinic acid was first identified in urine by Baker, H., Frank, O., Pasher, I., Hutner, S. H. and Sobotka, H., in 1960 (Clin. Chem. 6, 572, 1960).

4. Indole-3-acetic acid was recognized as the principal auxin of higher plants, and was prepared by Johnson and Crosby in 1963 (J. Org. Chem. 28, 1246, 1963). It was first identified in urine in 1964 by Seifer, A. and Gerstenfeld, S., (Clin. Chem. 10, 321, 1964).

A study of the literature revealed that the scientists mostly ignored indole and its derivatives contained in urine, feces and blood plasma. In the *Textbook of Organic Chemistry*, by E. Wertheim (1939 at pages 725-726) the following explanation for the formation of Indican was given:

"Detoxication.—Protein matter which escapes digestion in the small intestine normally undergoes bacterial putrefactive changes in the large intestine. A great number of substances, some of which are toxic in their nature, are formed as a result of the complete breakdown which takes place during this action. Among these are fatty acids, indole, skatole, phenol, phenylacetic and phenylpropionic acids, carbon dioxide, hydrogen sulfide, methane, ammonia, hydrogen, and other compounds.

"Indole and skatole are absorbed by the intestine and later eliminated in part in the urine, after being oxidized to indoxyl and skatoxyl respectively, and combined with sulfuric acid:

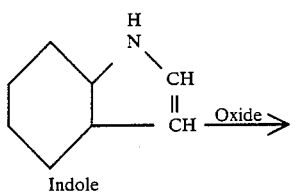

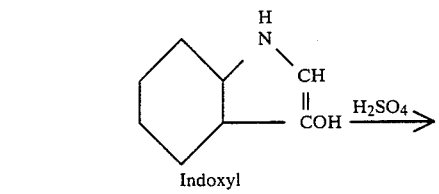

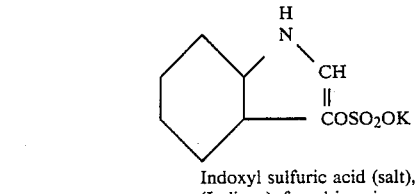

Indoxyl sulfuric acid (salt), (Indican), found in urine

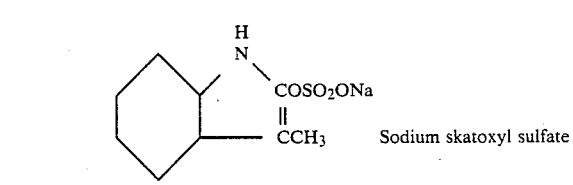

Sodium skatoxyl sulfate phenol and cresol are eliminated in the urine partly free, partly conjugated with sulfuric acid:

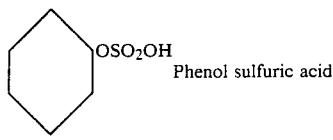
Phenol sulfuric acid

"The amount of indican the urine gives in approximate index of the protein purification in the intestine."

The *Physicians' Desk Reference* (PDR) has 34 categories of dermatological preparations, including antibacterial and antifungal. However, there is no "antiviral" heading. The three anti-inflammatory agents listed all utilize a corticosteroid as their active ingredient. However, they do not heal the inflammations or lesions produced by the Herpes viruses.

None of the listed salves, ointments, foams, lotions or other materials intended for topical use employ Indole or derivatives of Indole such as Indomethacin, Tryptophan, Indole-3-propionic acid, Indole-3-acetic acid, Indole-2-carboxylic acid or Tryptophol. *Mercks Manual of Diagnosis and Therapy* suggests that for Herpes Simplex I and II, topical use of Idoxuridine (IDU) for herpetic keratitis (eye infection) may be effective. In addition, Mercks mentions Acyclovir as having shown promise in the treatment of Herpes lesions.

For other Herpes lesions, Mercks suggests 'drying lotions' such as Camphor Spirit or 70% alcohol. For Herpes Zoster, Mercks states: "there is no known specific therapy."

Proteolytic enzymes which attack and degrade proteins, while claimed to have anti-inflammatory effects have no effect on Herpes inflammations or lesions.

Hormones which directly or indirectly cause the adrenal cortex to produce and secrete sterois, represent another class of anti-inflammatory compounds. However, no known hormones have produced a satisfactory response in the treatment of Herpes inflammations or lesions.

Inglot *TOPICAL TREATMENT OF CUTANEOUS HERPES SIMPLEX IN HUMANS WITH THE NON-STEROID ANTIINFLAMMATORY DRUGS: MEFENAMIC ACID AND INDOMETHACIN IN DIMETHYLSULFOXIDE*, Archivum Immunologiae et Therapiae Experimentalis, 18, 555 (1971) used Indomethacin, an Indole-containing compound, and Mefenamic acid a non-Indole containing compound in a highly toxic carrier, dimethylsulfoxide (DMSO) to treat Herpes sores. Inglot chose the carrier DMSO because it was a vehicle which ". . . facilitates their penetration into the skin." Inglot states that she did not test the DMSO carrier alone on Herpes sores.

Eckert, U.S. Pat. No. 4,263,313, issued on Apr. 21, 1981 discloses a carrier for Indomethacin to be applied to the skin of rheumatically affected patients. The express objective of the carrier is to improve the absorption of the active compound into the skin. Eckert's objective is to get Indomethacin into the body without traversing the intestinal tract, not to treat a disease of the skin.

Silber, U.S. Pat. No. 3,629,412 issued on Dec. 21, 1971, teaches use of Indomethacin as a topical ingredient with methylsalicylate (oil of wintergreen). Silber's primary objective, like Eckert is to get Indomethacin into the body without traversing the alimentary tract, though he suggests topical effectiveness on skin inflammations generally.

Prior to this invention, there were no antiviral agents in a non-toxic base which were free from harmful side-effects and that were effective in the treatment and alleviation of pain and the inflammatory response caused by Herpes virus.

Food and Indole Derivatives

There are 22 amino acids using in the human body as the primary components for proteins. Eight of these amino acids, tryptophan, leucine, lysine, methionine, pheynylalanine, isoleucine, valine and threonine are known as the "essential" amino acids. These "essential" amino acids must be supplemented to the human diet, the human body uses these essential amino acids as raw materials to produce proteins and other chemicals.

Tryptophan is the only indole derivative among the "essential" amino acids and is responsible in the human system for production of the following indole derivatives:

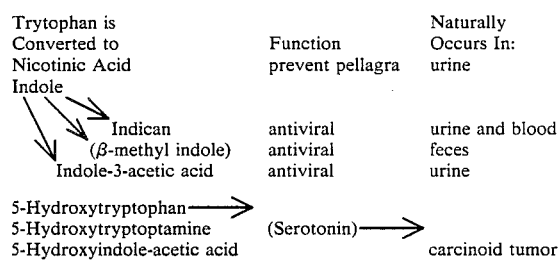

Indomethacin

Indomethacin is a synthetic, non-steroidal compound also containing the Indole structure. This differentiates it from compounds such as salisylates, corticosteroids, phenylbutazone-like compounds and colchicine. Indomethacin is slightly soluble in ethyl acohol, chloroform, ether, and acetone. It is substantially insoluble in cold water cod liver oil and caster oil. The PDR lists Indomethacin as a drug for oral use. There is no discussion or suggestion of topical use for any purpose. Indomethacin and other Indole derivatives were patented on Dec. 15, 1964 by Shen in U.S. Pat. No. 3,161,654, now expired. The Shen Patent sets forth procedures for producing these materials.

The Merck Index describes Indomethacin as an anti-inflammatory, anti-pyretic, analgesic agent. Indomethacin is well known to physicians under the Merck trademark Indocin. Merck supplies the drug in pill form, containing 25, 50 and 75 milligrams of the active ingredient.

*The Modern Drug Encyclopedia*, edited by Arthur J. Lewis, MD states that Indomethacin ". . . orally administered for rheumatoid arthritis, rheumatoid (anklosing) spondylitis, degenerative joint diseases (osteoarthritis) of the hips, knees and shoulders, and for gout. During the interval phase of gouty arthritis, Indomethacin together with adequate doses of a uricosuric agent may relieve pain and prevent the recurrence of acute attacks.

"The adverse reactions of Indomethacin on humans may include headache, dizziness, lightheadedness, syncope, drowsiness, convulsions, peripheral neuropathy, diarrhea, single or multiple ulcerations, bleeding in gastrointestinal tract without obvious ulcer, elevated blood pressure, agiitis, skin rashes, and acute respiratory distress including sudden dypsnea and asthma."

Nicotinic acid

Nicotinic Acid prevents Pellagra which is associated with a trytophan deficiency. Pellagra is characterized by
a. Dermatitis,
b. Diarrhea,
c. Demetia and
d. Death; a certain outcome in untreated patients.

Indican

Indican (Potassium indoxyl sulfate) naturally occurs in urine and blood plasma of humans and other mammals. Indican was first prepared as a potassium salt from potassium indoxyl and potassium bisulfite by Baeyer in 1881. At about that time, the Baeyer Company developed indigio dyes, in that context synthetic indican was investigated. Indican forms light brown crystals which decompose at 179°-180° C. with sublimation. Indican is very soluble in water and practically insoluble in cold alcohol. indican is safely stored at temperatures below 0° C.

SUMMARY OF THE INVENTION

This invention is directed toward a compositionfor topical use in treatment of skin disease typically caused by a virus of the Herpes type. The active ingredients of the compositions are Indole and derivatives of Indole such as Indomethacin, Indican Tryptophan, Indole-2-carboxylic acid, Indole-3-propionic acid, Indole-3-acetic acid and Tryptophol when used in a base such as petrolatum or DESITIN ® brand ointment, or an equivalent composition which limits absorption of the active ingredient through the skin, thereby maintaining a high concentration of the active ingredient in close contact with the affected area and limiting the side effects of the active ingredient. DESITIN ® is a registered Trademark of the Leeming Div. of Pfizer Inc., 235 E. 42nd St., New York, N.Y., 10017 for an over-the-counter salve used to sooth babies skin.

Herpes, the Illness and its Treatment

Herpes is spreading in the United States at an alarming rate. It is estimated that between 20 and 35 million Amercians already have the disease and another half million are expected to contract it each year.

The first symptoms of Herpes infections are commonly a sensitivity or inflammation consisting of a burning sensation, tingling, itching and/or a minor rash on the skin. As used herein, the term skin includes oral, genital and anal mucosa. Some individuals also note pains in the lower back and legs. These symptoms are known as the prodome. Within a few hours to up to two days, a few red marks will appear on the involved area. After a few more hours those marks become raised and full of fluid, looking more like blisters on a red base. The blisters are small, usually only 2-5 mm wide, and are often clustered. The blisters rupture, emitting an exudate, and the ulcers are usually very painful. The individual may also experience low fever, malaise, muscular aches, vaginal burning and/or discharge in a women, pain and itching of the penis in a man, frequent urination, and swelling of the thigh and neck/lymph glands. These last symptoms are more pronounced if it is an individual's first outbreak of Herpes. The lesions associated with the initial outbreak often last 2-6 weeks.

Between 50 and 67% of Herpes victims experience recurrence of the sores. This can happen any time; days, months or even years after the initial outbreak. It is thought that the virus lodges in nerve cells until it is triggered to renewed activity by some types of stress—emotional, menstrual, dietary or physical—which varies from person to person. Recurrences tend to be confined to one area, are less intense, and are shorter in duration, about 8-14 days. Symptoms and sores are similar to those experienced during the primary infection, though often less severe.

Although Herpes sores in most cases are merely unsightly and acutely uncomfortable, the exudate poses a severe transmission problem when brought in contact with the mucous membranes (mouth, genitalia, eyes) of another person, or the patient himself.

In one case, Herpes lesions can be life threatening; a newborn infant, born of a mother exhibiting genital Herpes lesions, stands a high probability of contacting the disease. Herpes in the newborn can result in death or brain damage.

Therefore, a treatment which prevents the formation, or promotes the healing of Herpes lesions not only helps the individual patient but also reduces the transmissibility of the disease on the effected patient, and to others.

*The Medical Dictionary*, edited by Dorland defines an inflammation as "a localized protective response elicited by injury or destruction of tissues which serves to destroy, dilute or wall off both the injurious agent and the injured tissue. It is characterized in the acute form by the classical sequence of pain, heat, redness, swelling and the loss of function. Histologically, it involves a complex series of events including dilation of the arterioles, capillaries and venules with increased permeability and blood flow, exudation of fluids, increasing plasma protenis, and leukocytic migration into inflammatory focus."

The inflammatory response is any response characterized by inflammation as described above. Inflammation of the tissues may be caused by bacteria or viruses or irritation by mechanical, chemical agents or by irradiation. This specification discussing inflammatory responses caused by viruses; however, this discussion is also applicable when applied to inflammatory responses caused by bacteria.

Viruses

At present, we know that a number of different viruses possess the property of infectivity, and that they differ from bacteria in that they lack a cell wall and the related enzyme systems. Viruses are classified on the basis of either Deoxyribonucleic acid (DNA) or Ribonucleic acid (RNA). In most cases the known antiviral agents that affect DNA virus replication have no effect on RNA viruses, and vice-versa. There are many strains of the viruses, and the differences between the strains are detected on the basis of immunological response.

DNA viruses include the following:
a. Poxviruses (e.g. vaccinia, variola, myxoma)
b. Herpes Viruses. There are a number of known Herpes viruses, although there may be still more Herpes viruses which are not presently known. The following table provides a brief summary of the known viruses:

| NAME OF VIRUS | MEDICAL NAME OF DISEASE | COMMON NAME OF DISEASE |
|---|---|---|
| Herpes Simplex I | Varicella | Chickenpox |
| | Herpes Simplex | Fever Blisters |

| NAME OF VIRUS | MEDICAL NAME OF DISEASE | COMMON NAME OF DISEASE |
|---|---|---|
| Herpes Simplex II (HSV-2) | Herpes Genitalis | Genital Herpes |
| Varicella Zoster (VZ) Zoster | Herpes Zoster | Shingles |
| VZ (Zoster) may cause Chickenpox in non-immune children and Shingles in partially immune adults. | | |
| Epstein Barr (ESBV) EB Herpes virus | Infectious Mononucleosis | Mononuleosis (Mono) |
| Cytomegalo | Jaundice Hepatosplenomegaly | Jaundice | c. Adenovirus. Many strains are known, they are believed to be responsible for acute respiratory diseases.

d. Papoviruses such as papilloma, polyome and SV 40 in Rhesus monkeys.

RNA Viruses include the following:

a. Myxoviruses. These cause influenza A, B, and C, mumps, swine influenza and fowl plague.

b. Arboviruses. These cause equine encephalomyelitis, Sindbis, yellow fever and Semliki Forest.

c. Picornaviruses. These cause Polio, Coxsackie, and enteric cytopathogenic human orphans (ECHO)

d. Rhinoviruses. These are a subgroup of Picornaviruses associated with the common cold of man.

DETAILED DESCRIPTION OF THE INVENTION

The present invention relates to compounds which will safely and effectively treat the Herpes symptoms of inflammation and lesions when applied to skin affected by the Herpes virus. The following compounds were tested over a wide range of concentrations ranging from pure compounds to 0.1%. Whenever a carrier or base was used, a non-toxic material was utilized of a type which was believed would have the dual functions of:

(a.) delaying absorption through the skin to maintain the highest concentration of the comound on the surface of the diseased skin, and (b.) delaying absorption through the skin to minimize possible side effects such as those which have been documented for Indomethacin, discussed in the Background of the Related Art.

a. acetylsalicylic acid (aspirin)

b. 4-Butyl-1,2-diphenyl-3,5-pyrazolidinedione (Phenylbutazone)

c. 2-[(2,3-dimethylphenyl)amino]-benzoic acid (Mefenamic acid)

d. alpha($\alpha$)-methyl-4-(2-methylpropyl-benzene-acetic acid (Ibuprofen)

e. 1-(4-chlorobenzoyl)-5-methyl-2-methyl-1H-indole-3-acetic acid; or otherwise known as: 1-(p-chlorobenzoyl)-5-methoxy-2-methylindole-3-acetic acid (Indomethacin)

f. Indole-3-ethanol (Tryptophol)

g. Indole-2-carboxylic acid (purchased from the Sigma Chemical Company, St. Louis, MO.)

h. Indole-3-propionic acid i. Indole-3-acetic acid j. L-alpha-amino-3-indole propionic acid (L-Tryptophan)

k. Indole-3-sulfate potassium salt (urinary indican)

It was found that aspirin, phenylbutazone, mefanamic acid and Ibuprofen, also known as Motrin, were ineffective in the in-vivo topical treatment of Herpes inflammations and sores.

However, it was found that all the compounds containing an Indole group and Indole itself were effective, though not uniformly effective, in controlling pain and rapidly healing lesions and suppressing inflammations caused by Herpes viruses, and the lesions and inflammations believed to be caused by other DNA viruses.

In addition, further experimental investigation of indole and its derivatives has led to the following conclusions:

1. Indole and its derivatives contained in urine, feces and blood plasma are the antiviral agents which disinfect the urinary and alimentary systems of the human body.

2. Indole and its derivatives promote healing and prevent the outbreak of Herpes Simplex I and II lesions.

3. When Indomethacin or Indican are placed on the lips or other areas of the mouth, it was observed that the Indican or Indomethacin was inadvertently swallooed and passed through the digestive tract. No adverse side effects were realized after long-term testing.

4. In addition, when Indomethacin and/or Indican were placed on bleeding lesions, small amounts of Indican and/or Indomethacin were absorbed into the blood. No adverse side effects were observed over long-term testing.

It was observed that Indole and its derivatives suppressed the symptoms of Angina by changing the metabolism of the human body. It is believed that Indole and its derivatives, especially Indican and Indomethacin, are primary metabolic regulators of the human immune system and may prove useful in the treatment of heart disease as well as in the treatment of carcinogenic tumors.

Preparation of Indican-Desitin ointment of concentration of 1%

The coarse light brown crystaline indican is ground to fine powder which by passed through a 200 mesh sieve. This procedure is preferably done at a temperature below 0° C. One gram of the indican powder is then mixed with 99 grams of DESITIN®, or the equivalent salve formulation. The mixture is then placed in a water bath at a temperature of 40°–55° C., and thoroughly mixed. Indican dissolves in the cod liver oil which is contained in DESITIN® and after cooling forms a homogeneous Indican-Desitin ointment. The mixing and formulation of the ointment is finished in approximately 10 minutes. From a practical manufacturing viewpoint, the low viscosity, warm ointment should then be placed in tubes and cooled to room temperature. Instead of DESITIN® ointment, the following mixture can be used:

Approximately 400 grams Zinc Oxide, from 80 to 150 grams of talc powder, 90 to 100 grams of lanolin, 100 to 140 grams of petrolatum, and 200 to 320 grams of cod liver oil. The exact ratio of these components must be adjusted depending on the viscosity of the petrolatum and the quality of the lanolin, talc and cod liver oil so that the ointment does not bleed, or become powdery.

In the *Physican's Desk Reference,* (PDR) *for Non-Prescription Drugs,* 7th Edition, 1986 at pages 565 through 566 the components of DESITIN® ointment are described as:

"[A] Combination of zinc oxide (40%), cod liver oil (high in Vitamins A & D), and Talc in a petrolatum-lanolin base suitable for topical application."

The specific proportions of cod-liver oil, talc, lanolin and petrolatum are not disclosed. As discussed above, each batch must be emperically adjusted so that the ointment does not bleed. One reason for adjusting the proportions of the ointment is that the petrolatum may be very stiff, almost wax-like in one batch and very fluid in another batch. Also, the grain size of the Zinc Oxide and Talc may vary from batch to batch. DESITIN® has been chemically analyzed by the inventor to arrive at the approximate range of proportions listed above.

For Indican ointment, the preferred base, is approximately 400 grams Zinc Oxide, 80 grams talcum, 90 grams lanolin, 100 grams petrolatum and 320 grams cod liver oil. These components are mixed thoroughly and form a base for the indican ointment. Since every indole derivative has different crystaline structure and therefore different absorption capacity of the ingredients forming the base must be adjusted to the desired viscosity of the ointment.

The active compound, if solid, should be ground to pass 200 mesh. The following salves are typical of those which can be formulated using the above described base.

Salves

Salve Formulation No. 1
- 30 grams Indican (3%)
- 820 grams petrolatum
- 150 grams 95% ethyl alcohol (ethanol)

Salve Formulation No. 2
- 10 grams Indican (1%)
- 970 Grams DESITIN® brand ointment or the equivalent.

In place of DESITIN® the following mixture may be used.
- approximately 400 grams Zinc Oxide
- approximately 100 grams petrolatum
- approximately 90 grams lanolin
- approximately 80 grams talcum
- approximately 320 grams cod-liver oil
- approximately 1000 grams Salve formulation No. 3
- 10 grams Indican (1%)
- 130 grams ethanol
- 860 grams petrolatum Salve Formulation No. 4
- 500 grams Indican (50%)
- 500 grams DESITIN® brand ointment or the equivalent Salve Formulation No. 5
- 10 grams Tryptophan (1%)
- 990 grams DESITIN® brand ointment or the equivalent Salve Formulation No. 6
- 50 grams Indole-3-acetic acid (5%)
- 150 grams propylene glycol
- 800 grams petrolatum Salve Formulation No. 7
- 10 grams Indomethacin (1%)
- 990 grams DESITIN® brand ointment or the equivalent Salve Formulation No. 8
- 30 grams Indomethacin (3%)
- 970 grams DESITIN® brand ointment or the equivalent.

Salve Formulation No. 9
- 500 Indomethacin (50%)
- 500 grams DESITIN® brand ointment or the equivalent salve formulation.

In all formulations the ingredients are mixed thoroughly to assure uniform distribution of the primary active ingredient throught the base. The percentage concentration of the primary ingredient is listed adjacent to the ingredient. Since suggested courses of treatment will require concentrations less than those listed above, the concentrations of the primary active ingredient may be reduced simply by reducing the proportionate amount used in the preparation of the salve. For instance, in salve No. 1, Indican has a concentration of 3%. This concentration can be reduced to 1% simply by reducing the weight of Indican from 30 grams to 10 grams and simultaneously increasing the weight of petrolatum from 820 to 840 grams.

Physicians and other professionals may, at the risk of some side effects which may include local skin irritation, apply the pure Indole or Indole derivatives, powder or liquid, directly to the lesion.

Solutions

Solution Formulation No. 1
- 10 grams Indomethacin (1%)
- 745 grams ethanol
- 245 grams water A 0.1% solution is formed by adding only 1 gram Indomethacin to the adjusted weights of water and ethanol.

In all formulations employing granular form of the active agent the ingredients must be mixed thoroughly to assure distribution of the active agent throughout the preparation.

TREATMENT

Facial Herpes

In the following instruction Indican and Indomethacin are used. However, Indomethacin is intended to be a reference drug only for these examples. Other Indole containing compounds can be substituted for Indomethacin, with various degrees of effectiveness.

Clean the lesion or sensitive area with either soap and water, a 1% Indomethacin solution, or a low vacuum, dry and apply three percent Indican or Indomethacin salve, repeat every 4–6 hours until healing is observed. Then continue with 1% Indican or Indomethacin salve until healing is substantially complete. Continue applying the salve at a 0.1% concentration every 12 hours for three days to prevent recurrence.

Genital Herpes

Clean the lesion or sensitive area with either soap and water, 1% solution, and/or vacuum. Dry, and apply three percent salve. Repeat every four hours until itching, suppressed by the salve, does not re-occur. Then, extend the time periods between treatments until healing is observed.

Continue treatments with 1% Indomethacin. After healing is substantially complete, continue with 0.1% salve twice a day for four days to prevent recurrence. Lightly applied, regularly changed dressings may be used to protect clothing.

While the salves and process of this invention do effectively prevent and treat the external symptoms of Herpes infection, in no sense is it claimed that the treatments set forth, cure the patient of the underlying disease, though in some cases they may. In fact recurrence in the same or other location is possible or likely under those stimuli which might cause any dormant Herpes virus in the body to become active. In the case where the salve is used to suppress symptoms of burning which occur at the onset of an episode, that is, an event which if untreated would develop into a lesion. Then the recurrence of the burning symptoms become less and less frequent.

EXAMPLE 1

Herpes Simplex I (Cold Sore)

Day 1. At 10:00 a.m., the patient developed a Herpes Simplex I (Cold Sore) in the corner of his mouth. At 11:00 p.m., the sore was dried with a soft tissue and the sore was covered with an ointment containing 1% Indican in a DESITIN ® base.

Day 2. At 5:25 a.m., the patient noticed that healing of the lesion had occurred, more ointment was added to the lesion. Three hours later, the ointment was washed away with soap and water and the lesion was dried with a soft tissue. The lesion was again covered with a 1% Indican ointment and the procedure was repeated every 3 to 4 hours. At 8:30 p.m., the sore began to appear dry.

Day 3. At 6:30 a.m., the sore was covered with a small scab. The scab was covered every 6 hours with the 1% Indican ointment.

Day 4. The lesion was dry, however, since it was located in the corner of the mouth, whenever the patient began eating, the new skin at the corner of the mouth tore. A small amount of bleeding was noticed, however, the bleeding healed very quickly. After the fourth day, the lesion healed completely.

EXAMPLE 2

Herpes Simplex II (Genital Herpes)

1. The patient developed a Herpes Simplex II, Genital Herpes, lesion on the prepuce of his penis. The following treatment was administered: Liquid and pus in the lesion was removed with a vacuum pump which applied a vacuum of about 25 inches Hg to the sore. All liquid was drained from the lesion.

2. The dry sore was then covered with an ointment containing 1% Indican in a DESITIN ® base ointment. After approximately 20 minutes, the discomfort, including itching and burning was relieved.

3. Four hours later, the itching and burning sensation began to return to the area immediately surrounding the sore. The patient was at work so he cleansed the sore with a solution containing a 1% Indomethacin in alcohol. The lesion was then covered with a 1% Indican ointment. As healing progressed, the intervals of discomfort occurred about every six to eight hours.

4. The procedure was repeated over a period of 4 days after which the lesion completely healed.

To clean the sore, the 1% Indomethacin-alcohol solution may be replaced with a soap and water solution. However, a Herpes sore in the first stage of development is sensitive and full of liquid. Accordingly, the preferred procedure is to remove the liquid with a vacuum pump. Since each lesion may be in a different stage of inflammation at the time of treatment, the patient may selectively alter the above described treatment. If the sore is highly inflamed, a longer treatment period, using a higher concentration of Indican in the ointment may be required.

EXAMPLE 3

(Herpes Simplex I)

Day 1. The patient developed a Herpes Simplex I sore on his left upper lip at approximately 9:00 a.m. The sore was cleansed with soap and water. In order to accelerate healing of the sore, liquid from the sore was removed with a vacuum pressure of about 25 inches of Hg.

Step 1. The sore was treated with an ointment containing 1% Indomethacin in a DESITIN ® base ointment for 90 minutes.

Step 2. At 11:30 a.m., the sore was again cleansed with soap and water and dried with a soft tissue. Then, the sore was treated with an ointment containing 1% Indole-2-Carboxylic Acid in a DESITIN ® base ointment. After 5 hours (4:30 p.m.), the Indole-2-Carboxylic Acid ointment was removed from the sore, and the sore was cleaned with soap and water and dried with a soft tissue. It was observed that there was significant healing of the sore at that time.

Step 3. The clean sore was treated with an ointment containing 1% Tryptophol (Indole-3-ethanol) in a DESITIN ® base ointment. After five hours, (9:30 p.m.), the sore was cleaned with soap and water and dried with a soft tissue. The sore was almost completely healed.

Step 4. Second Day The clean sore was treated with an ointment containing 1% Indole-3-Acetic Acid in a DESITIN ® base ointment. After approximately seven-and-one-half hours (5:00 a.m.) the sore was cleaned with soap and water and dried with a soft tissue there was a little improvement.

Step 5. The cleaned dry sore was treated with an ointment containing 1% Indole-3-Propionic Acid in a DESITIN ® base ointment. The treatment was repeated every 4 to 6 hours. At 11:00 p.m., (after 18 hours), the sore disappeared. However, a red spot at the location of the sore was treated for another 24 hours to be sure that the sore was completely healed.

EXAMPLE 4

(Herpes Simplex II)

Day 1. The patient developed a Herpes Simplex II (Genital Herpes) lesion on the prepuce of his penis. The sore was treated with an ointment containing a one-to-one mixture of one of the following:

a. 1% Indomethacin in DESITIN ® base ointment and, b. 1% of Indican in DESITIN ® base ointment.

The treatment described in Example 2 was administered until the lesion was complete healed.

EXAMPLE 5

(Preventative Treatment of Herpes Simplex I and II Lesions)

The outbreak of Herpes Simplex I and II lesions may be prevented when the patient feels the itching and burning on an area of skin which is susceptible to inflammation caused by Herpes virus according to the following steps:

1. Apply vacuum of about 25 inches Hg on the area of itching or burning for approximately one minute.

2. Apply a salve containing a 1 to 3% concentration of Indomethacin or Indican in a DESITIN ® base ointment.

The itching and burning should immediately disappear.

3. Repeat Step 1 whenever itching and burning reoccur.

In most cases, the outbreak of a Herpes lesion is prevented.

Having described my invention it will be clear that many changes and modifications can be made thereto without altering the spirit or the scope thereof, and that all such changes are contemplated as falling within the scope of the following claims.

I claim:

1. A salve formulation for topical treatment of inflammations and lesions of the human skin due to Herpes type virus which includes an active ingredient in a concentration of at least 0.1% by weight, said active ingredient selected from the group consisting of:
   Indomethacin,
   Indole,
   Indican,
   Tryptophol,
   L-Tryptophan,
   Indole-2-carboxylic acid,
   Indole-3-propionic acid, and
   Indole-3-acetic acid;
said active ingredient is suspended in a carrier comprising:
   Zinc Oxide in a concentration of approximately 40% by weight,
   petrolatum,
   lanolin,
   talc, and
   Cod-liver oil.

2. The formulation of claim 1, wherein said carrier is DESITIN ® brand ointment.

3. The formulation of claim 1, wherein said active ingredient comprising a concentration of 0.1% to 50% by weight of said salve formulation.

4. The formulation of claim 2, wherein said active ingredient comprising a concentration of 0.1% to 50% by weight of said salve formulation.

5. The formulation of claim 1, wherein said active ingredient comprises a concentration of 0.1% to 3% by weight of said salve formulation.

6. The formulation of claim 2, wherein said active ingredient comprises a concentration of 0.1% to 3% by weight of said salve formulation.

7. The formulation of claim 1, wherein said active ingredient comprises a concentration of 0.1% by weight of said salve formulation.

8. The formulation of claim 2, wherein said active ingredient comprises a concentration of 0.1% by weight of said salve formulation.

9. The formulation of claim 1, wherein said active ingredient comprises a concentration of 3% by weight of said salve formulation.

10. The formulation of claim 2, wherein said active ingredient comprises a concentration of 3% by weight of said salve formulation.

11. The formulation of claim 1, wherein said carrier comprises:
    Zinc oxide in a concentration of approximately 40% by weight,
    petrolatum in a concentration of approximately 10% to 14% by weight,
    lanolin in a concentration of approximately 8% to 10% by weight,
    talc in a concentration of approximately 8% to 12% by weight, and
    Cod-liver oil in a concentration of approximately 21% to 32% by weight.

12. The formulation of claim 3, wherein said carrier comprises:
    Zinc oxide in a concentration of approximately 40% by weight,
    petrolatum in a concentration of approximately 10% to 14% by weight,
    lanolin in a concentration of approximately 8% to 10% by weight,
    talc in a concentration of approximately 8% to 12% by weight, and
    Cod-liver oil in a concentration of approximately 21% to 32% by weight.

13. The formulation of claim 5, wherein said carrier comprises:
    Zinc oxide in a concentration of approximately 40% by weight,
    petrolatum in a concentration of approximately 10% to 14% by weight,
    lanolin in a concentration of approximately 8% to 10% by weight,
    talc in a concentration of approximately 8% to 12% by weight, and
    Cod-liver oil in a concentration of approximately 21% to 32% by weight.

14. The formulation of claim 7, wherein said carrier comprises:
    Zinc oxide in a concentration of approximately 40% by weight,
    petrolatum in a concentration of approximately 10% to 14% by weight,
    lanolin in a concentration of approximately 8% to 10% by weight,
    talc in a concentration of approximately 8% to 12% by weight, and
    Cod-liver oil in a concentration of approximately 21% to 32% by weight.

15. The formulation of claim 9, wherein said carrier comprises:
    Zinc oxide in a concentration of approximately 40% by weight,
    petrolatum in a concentration of approximately 10% to 14% by weight,
    lanolin in a concentration of approximately 8% to 10% by weight,
    talc in a concentration of approximately 8% to 12% by weight, and
    Cod-liver oil in a concentration of approximately 21% to 32% by weight.

16. A salve formulation for topical treatment of inflammations and lesions of the human skin due to Herpes type virus which includes Indican in a concentration of 0.1% to 3% by weight as the active ingredient which is suspended in a carrier comprising:
    Zinc oxide in a concentration of approximately 40% by weight,
    petrolatum in a concentration of approximately 10% to 14% by weight,
    lanolin in a concentration of approximately 8% to 10% by weight,
    talc in a concentration of approximately 8% to 12% by weight, and
    Cod-liver oil in a concentration of approximately 21% to 32% by weight.

17. The formulation of claim 16 wherein said carrier is DESITIN ® brand ointment.

18. A method for topical treatment of inflammations and lesions of the human skin due to Herpes type virus which includes the step of applying to the surface of the skin the salve formulation recited in claim 1.

19. A method for topical treatment of inflammations and lesions of the human skin due to Herpes type virus which includes the step of applying to the surface of the skin the salve formulation recited in claim 16.

20. A method for topical treatment of inflammations and lesions of the human skin due to Herpes type virus which includes the step of applying to the surface of the skin the salve formulation recited in claim 17.

21. A method for topical treatment of inflammations and lesions of the human skin due to Herpes type virus which includes the steps of applying to the surface of the skin a therapeutically effective amount of an active ingredient selected from the group consisting of:
Indole,
Indican,
Tryptophol,
L-Tryptophan,
Indole-2-carboxylic acid,
Indole-3-propionic acid, and
Indole-3-acetic acid.

22. The method recited in claim 21, wherein said active ingredient is present in a formulation which includes a pharmaceutically acceptable carrier.

23. The method recited in claim 22, wherein said active ingredient comprises a concentration of at least 0.1% by weight of said formulation.

24. The method recited in claim 22, wherein said active ingredient comprises a concentration from about 0.1% to about 50% by weight of said formulation.

25. The method of claim 22, wherein said active ingredient comprises a concentration of from about 0.1% to about 3% by weight of said formulation.

26. The method of claim 22, wherein said active ingredient comprises a concentration of about 0.1% by weight of said formulation.

* * * * *